US008788291B2

(12) United States Patent
Srinivasan et al.

(10) Patent No.: US 8,788,291 B2
(45) Date of Patent: Jul. 22, 2014

(54) SYSTEM AND METHOD FOR ESTIMATION OF MISSING DATA IN A MULTIVARIATE LONGITUDINAL SETUP

(75) Inventors: Soundararajan Srinivasan, Mountain View, CA (US); Priya Kohli, College Stattion, TX (US)

(73) Assignee: Robert Bosch GmbH, Stuttgart (DE)

( * ) Notice: Subject to any disclaimer, the term of this patent is extended or adjusted under 35 U.S.C. 154(b) by 20 days.

(21) Appl. No.: 13/403,693

(22) Filed: Feb. 23, 2012

(65) Prior Publication Data
US 2013/0226613 A1 Aug. 29, 2013

(51) Int. Cl.
*G06Q 50/24* (2012.01)
*G06Q 50/22* (2012.01)

(52) U.S. Cl.
CPC ............... *G06Q 50/24* (2013.01); *G06Q 50/22* (2013.01)
USPC .................................. 705/3; 705/2

(58) Field of Classification Search
CPC .......................................... G06Q 50/22–50/24
USPC .......................................... 705/2–3
See application file for complete search history.

(56) References Cited

U.S. PATENT DOCUMENTS

| 5,463,548 | A | 10/1995 | Asada et al. |
| 5,704,018 | A | 12/1997 | Heckerman et al. |
| 2003/0233197 | A1 | 12/2003 | Padilla et al. |
| 2004/0083452 | A1 | 4/2004 | Minor et al. |
| 2006/0271300 | A1* | 11/2006 | Welsh et al. ............ 702/19 |
| 2007/0136035 | A1* | 6/2007 | Minor et al. ............ 703/2 |
| 2007/0174290 | A1 | 7/2007 | Narang et al. |
| 2008/0133275 | A1 | 6/2008 | Haug et al. |
| 2008/0256011 | A1 | 10/2008 | Rice |
| 2009/0024332 | A1 | 1/2009 | Karlov et al. |
| 2009/0164405 | A1 | 6/2009 | Yang et al. |
| 2010/0121615 | A1 | 5/2010 | Cunningham |

OTHER PUBLICATIONS

Beunckens, C., et al. "A Latent-Class Mixture Model for Incomplete Longitudinal Gaussian Data" Biometrics 64, Mar. 2008, pp. 96-105.*
Creemers, A., et al. "Generalized shared-parameter models and missingness at random" Statistical Modeling 2011; 11(4): pp. 279-310.*
Gottfredson, N. "Evaluating shared-parameter mixture models for analyzing change in the presence of non-randomly missing data" Dissertation of the University of North Carolina at Chapel Hill 2011.*
Cameletti et al., "Comparing air quality statistical models", Thesis, Mar. 14, 2011, pp. 1-53, Italy (53 pages).
Clement, "Statistical validation and spatio-temporal modelling of river monitoring networks," Ph.D thesis, 2007, pp. 1-267, Ghent University, Gent, Belgium (267 pages).

(Continued)

*Primary Examiner* — Sheetal R Rangrej
(74) *Attorney, Agent, or Firm* — Maginot, Moore & Beck

(57) ABSTRACT

A method for estimating values of missing data in partial sets of medical data includes generating a Gaussian mixture with a time-varying mean and time and lag varying covariances. The method generates the estimate for a missing datum with the Gaussian distribution having a selected mean and covariance corresponding to the time of the missing datum. An estimate of the missing datum is generated with reference to the mean of the Gaussian distribution conditioned on other medical data that are observed at the time of the missing datum.

17 Claims, 5 Drawing Sheets

(56) References Cited

OTHER PUBLICATIONS

Huang et al., "Estimation of Large Covariance Matrices of Longitudinal Data with Basis Function Approximations," Thesis, pp. 1-28, 2007, USA (28 pages).
Jo et al., "Regression Splines with Longitudinal DATA," Paper 143-2007, SAS Global Forum 2007, pp. 1-6, University of Medial Sciences, Little Rock, AR (6 pages).
Kong et al., "A modeling framework for the analysis of HPV incidence and persistence: A semi-parametric approach for clustered binary longitudinal data analysis," Statistics in Medicine, 2010, pp. 2880-2889, vol. 29, John Wiley & Sons, Ltd., USA (10 pages).
Leng et al., "Semiparametric Mean—Covariance Regression Analysis for Longitudinal Data," Journal of the American Statistical Association, 2010, pp. 181-193, vol. 105, No. 489, Theory and Methods, USA (13 pages).
Morris et al., "Some Solutions to the Missing Feature Problem in Data Classification, with Application to Noise Robust ASR," Paper, Department of Computer Science, University of Sheffield, United Kingdom, 1998 (4 pages).
Ni et al., "Markov Chain Monte Carlo Multiple Imputation for Incomplete ITS Data Using Bayesian Networks," Paper submitted for presentation and publication at the Transportation Research Record, Jul. 12, 2004, pp. 0-21, Georgia Institute of Technology, Georgia (22 pages).
Pan et al., "K-Nearest Neighbor Based Missing Data Estimation Algorithm in Wireless Sensor Networks," Journal Wireless Sensor Network, 2010, pp. 115-122, vol. 2, Scientific Research, China (8 pages).
Pang, "A Bayesian Dynamic Factor-Residual Model for Spatial Dependence in Longitudinal Data," Ph.D. thesis, Department of Politics, Princeton University, pp. 0-33, USA (34 pages).
Wu et al., "Nonparametric estimation of large covariance matrices of longitudinal data," Biometrika, 2003 (25 pages).
Zhang et al., "A Bayesian Semi-parametric Survival Model with Longitudinal Markers," Biometrics: Journal of the International Biometric Society, Jun. 8, 2009 (28 pages).
Faubel, Friedrich et al., "Bounded Conditional Mean Imputation with Gaussian Mixture Models: A Reconstruction Approach to Partly Occluded Features", Acoustics, Speech and Signal Processing, 2009, ICASSP 2009, IEEE International Conference on, IEEE, Piscataway, NJ, USA, Apr. 19, 2009, pp. 3869-3872 (4 pages).
Raghunathan, Trivellor E. et al., "A Multivariate Technique for Multiply Imputing Missing Values Using a Sequence of Regression Models", Statistics Canada, Catalogue No. 12-001, Jun. 2001, pp. 85-95, Retrieved from the Internet: URL:http://www.statcan.gc.ca/ads-annonces/12-001-x/5857-eng.pdf (11 pages).
Van Buuren, S. et al., "Multiple imputation of missing blood pressure covariates in survival analysis", Statistics in Medicine, Mar. 30, 1999, pp. 681-694, England, Retrieved from the Internet: URL:http://www.ncbi.nlm.nih.gov/pubmed/10204197 (14 pages).
Wikipedia, "Cholesky Decomposition", Wikipedia, Feb. 21, 2012, Retrieved from the Internet: URL:http://en.wikipedia.org/w/index.php?title=Cholesky decomposition&oldid=478131740 (5 pages).
Yuan, Yang C., "Multiple Imputation for Missing Date: Concepts and New Development (Version 9.0)", SAS SUGI Proceedings, 2000, pp. 1-13, Retrieved from the Internet: URL:http://support.sas.com/rnd/app/papers/multipleimputation.pdf (13 pages).
International Search Report and Written Opinion corresponding to PCT Application No. PCT/US2013/027354, mailed Dec. 9, 2013 (15 pages).

\* cited by examiner $$\begin{bmatrix} 1 & 0 & 0 & 0 & 0 \\ -\phi_0 & 1 & 0 & 0 & 0 \\ -\phi_1 & -\phi_0 & 1 & 0 & 0 \\ -\phi_2 & -\phi_1 & -\phi_0 & 1 & 0 \\ -\phi_3 & -\phi_2 & -\phi_1 & -\phi_0 & 1 \end{bmatrix} \begin{bmatrix} y_0 \\ y_1 \\ y_2 \\ y_3 \\ y_4 \end{bmatrix} = \begin{bmatrix} \varepsilon_0 \\ \varepsilon_1 \\ \varepsilon_2 \\ \varepsilon_3 \\ \varepsilon_4 \end{bmatrix}$$

$$T \quad \times \quad Y \quad = \quad \varepsilon$$

FIG. 5

$$Var(\varepsilon_n) = $$

| | $\varepsilon_0$ | $\varepsilon_1$ | $\varepsilon_2$ | $\varepsilon_3$ | $\varepsilon_4$ |
|---|---|---|---|---|---|
| $\varepsilon_0$ | $\sigma^2_0$ | | | | |
| $\varepsilon_1$ | | $\sigma^2_1$ | | | |
| $\varepsilon_2$ | | | $\sigma^2_2$ | | |
| $\varepsilon_3$ | | | | $\sigma^2_3$ | |
| $\varepsilon_4$ | | | | | $\sigma^2_4$ |

SYSTEM AND METHOD FOR ESTIMATION OF MISSING DATA IN A MULTIVARIATE LONGITUDINAL SETUP

TECHNICAL FIELD

This patent relates generally to the fields of medical information and patient management, and, more particularly, to methods and systems for estimating missing medical data for a patient when only partial data are available.

BACKGROUND

Many scientific and medical monitoring systems generate multivariate and longitudinal data. The term "multivariate" means that the monitoring system obtains data for multiple, dependent, variables for each subject of interest to the system. The term "longitudinal" means that the data is obtained for the multiple variables at multiple times during the monitoring process. One common example of a multivariate and longitudinal monitoring system is a patient health monitoring system. The patient health monitoring system monitors various attributes associated with the health of a patient, such as heart rate, blood pressure, blood sugar, temperature, weight, respiration, disease symptoms, and the like. The data for the attributes or variables associated with the patient may differ at the sample times so the system is a longitudinal data system, and the health monitoring system is multivariate because the monitoring system collects variable data corresponding to two or more attributes. A monitoring system can include an automated device that measures and collects the medical data for the multiple variables over time. Alternatively, the medical data can be collected during a series of medical exams performed by a healthcare provider.

A health care provider can diagnose various medical conditions and monitor the course of medical treatment over time using the multivariate longitudinal medical data. The medical data can, however, be partially incomplete at various times. For example, a set of medical data can include variables corresponding to respiration rate, heart rate, and temperature of a patient that are monitored over time. In some instances, at least one of the variables is not recorded at the same time as the other variables. For example, the heart rate and temperature of the patient are recorded one day, and the respiration rate and heart rate are measured on another day. Both sets of medical data are partially complete for the patient. Various methods exist for handling incomplete data sets, but all of the existing methods have limitations. One method of handling the missing data is to simply ignore medical records that are only partially complete, but this also ignores valuable medical data. Other methods, generally denoted as correlation methods, use a predetermined correlation model to estimate a value for the variable not sampled using the known values for the sampled variables. Correlation methods can suffer from bias and the correlation models are based on a large group of patients that may not represent an individual patient accurately. Still other methods include time based regression techniques that impute a value for the missing data based on medical data for the patient from other times. While the regression techniques can be useful in some cases, the regression techniques tend to generate values that correspond to a long-term average of a medical attribute and can ignore potential short term changes in the condition of the patient.

Patient health monitoring systems have a wide variety of uses in providing medical care to patients and monitoring chronic conditions. Some patient monitoring systems are used in the field of telemedicine and home health care. In a telemedicine system, a patient is geographically removed from the presence of a doctor or other healthcare provider. For example, the patient could be at home instead of on site at a healthcare facility. One or more telemedical devices enable the healthcare provider to monitor the health status of a patient and potentially diagnose and treat some medical problems without the need for the patient to travel to the healthcare facility. The use of telemedical systems has the potential to reduce the cost of healthcare, and to improve the quality of healthcare through increased patient monitoring.

While telemedicine systems have numerous advantages, one disadvantage relates to the aforementioned problem of missing medical data. While any medical monitoring system can generate incomplete medical data, the telemedical systems are more prone to missing data at various times since such systems rely on the patient to operate a monitoring device or provide medical information. In some instances, a partial set of medical data is generated at a given time while the data corresponding to one or more attributes are missing. For example, a patient in a telemedicine system may remember to check his blood pressure but forget to check his blood sugar level on a given day. As described above, existing systems and methods for handling missing medical data have limitations that present challenges to medical and scientific study of the partial data. Consequently, improvements to the analysis of partially complete multivariate longitudinal data would be beneficial.

SUMMARY

In one embodiment, a method for generating estimated data in a multivariate series of data corresponding to a plurality of times has been developed. The method includes retrieving data associated with a plurality of variables corresponding to a plurality of times from a memory with a controller communicatively coupled to the memory, detecting a missing datum and a time period of the missing datum corresponding to one variable in the plurality of variables and one time in the plurality of times in the retrieved data with the controller, generating data corresponding to a function of a mean of each of the plurality of variables with respect to time with the controller, identifying, with the controller, a plurality of random variable vectors with reference to the plurality of times, each random variable vector including a plurality of random variables that correspond to each of the plurality of variables, generating data corresponding to a covariance matrix of the plurality of random variable vectors with the controller, generating, with the controller, a conditional Gaussian mixture model corresponding to the one time of the missing datum with reference to the polynomial of the mean of each variable at the one time, the covariance matrix, and the data corresponding to at least one variable in the plurality of variables other than the one variable, identifying an estimated value for the missing datum with reference to the conditional Gaussian mixture model with the controller, and storing the estimated value for the missing datum in the memory with the controller to enable processing of the data associated with the plurality of variables corresponding to the plurality of times, the estimated value being stored with reference to the one variable and the one time of the missing datum.

In another embodiment, a system for generating estimated data in a multivariate series of data corresponding to a plurality of times has been developed. The system includes a memory configured to store recorded values of a plurality of variables corresponding to medical data of a patient generated at a plurality of times, an output device configured to display the recorded values for a healthcare provider, and a controller operatively connected to the memory and the output. The controller is configured to detect a missing datum corresponding to one variable in the plurality of variables and one time in the plurality of times in the recorded values in the memory, generate data corresponding to a polynomial of a mean of each of the plurality of variables with respect to time, identify a plurality of random variable vectors with reference to the plurality of times, each random variable vector including a plurality of random variables that correspond to each of the plurality of variables, generate data corresponding to a covariance matrix of the plurality of random variable vectors, generate a conditional Gaussian mixture model corresponding to the one time of the missing datum with reference to the polynomial of the mean of each variable at the one time, the covariance matrix, and the data corresponding to at least one variable in the plurality of variables other than the one variable, identify an estimated value for the missing datum with reference to the conditional Gaussian mixture model, store the estimated value for the missing datum in the memory with the controller to enable processing of the data associated with the plurality of variables corresponding to the plurality of times, the estimated value being stored with reference to the one variable and the one time of the missing datum, and generate a display of the recorded values of the plurality of variables and the estimated value for the missing datum with the output device.

BRIEF DESCRIPTION OF THE DRAWINGS

FIG. 5 is a matrix diagram depicting regression parameters for multiple of medical data.

FIG. 6 is a matrix diagram of variances of errors in the medical data identified in FIG. 5.

DETAILED DESCRIPTION

For the purposes of promoting an understanding of the principles of the embodiments described herein, reference is now be made to the drawings and descriptions in the following written specification. No limitation to the scope of the subject matter is intended by the references. The descriptions also includes any alterations and modifications to the illustrated embodiments and includes further applications of the principles of the described embodiments as would normally occur to one skilled in the art to which this document pertains.

Figure 1:
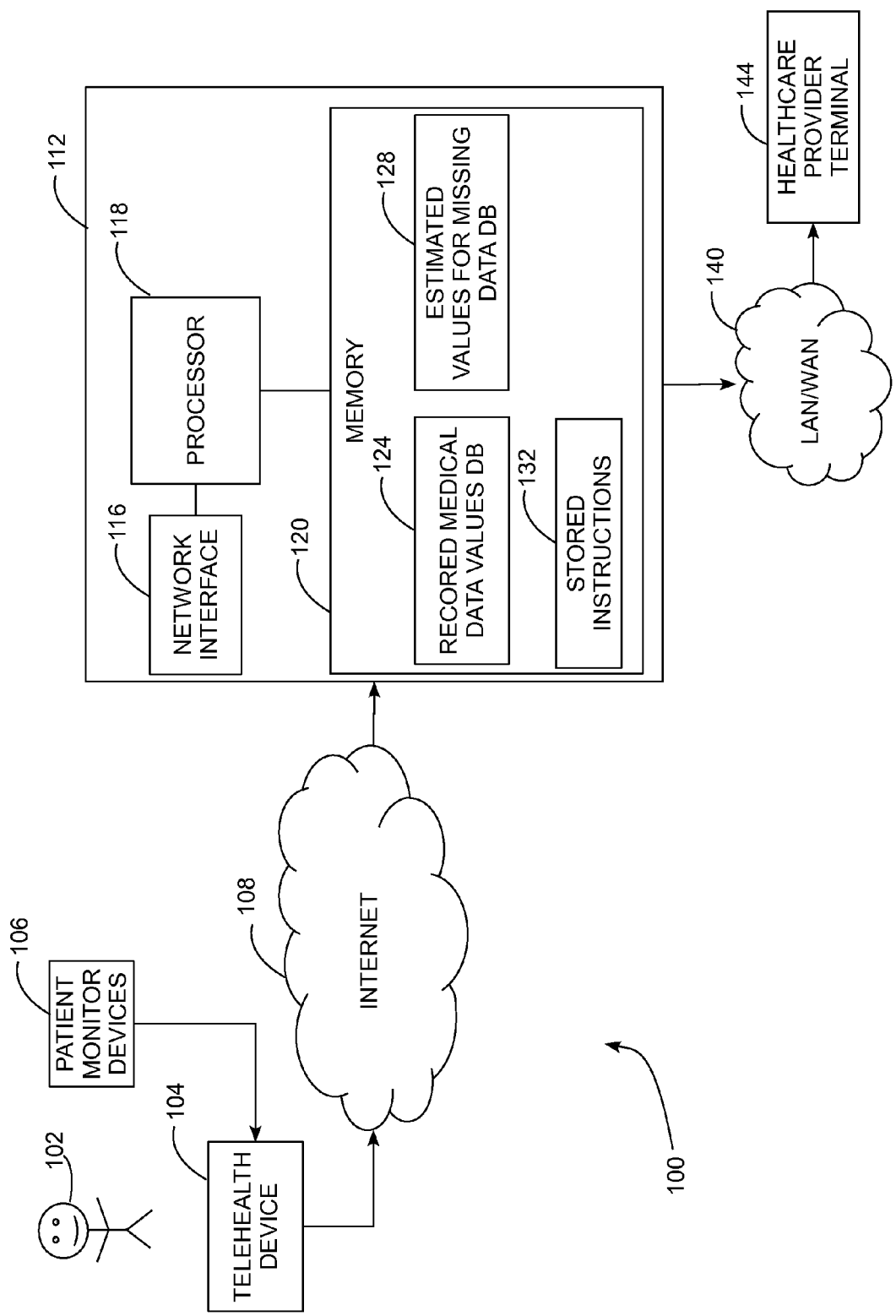
FIG. 1 is a diagram of a telehealth system.

FIG. 1 depicts a telehealth system 100 that collects health related information from a patient. The system 100 includes a telehealth device 104 that is operatively connected to a telehealth analysis system 112 through a data network 108, such as the Internet. The telehealth device 104 collects a variety of medical information from a patient 102, and sends the medical information to the telehealth analysis system 112 through the data network 108.

The telehealth device 104 includes a user interface with one or more input and output devices. In one embodiment, the telehealth device 104 includes a display screen that presents text, graphics, and control menus to the patient 102, and a touch screen input that accepts patient input and menu selections. Some alternative input and output devices include speech synthesizers and speech recognition inputs, and mechanical keypads and keyboards. The telehealth device 104 presents health related questions to the patient 102 on a daily basis or at regular intervals in accordance with medical treatment provided to the patient 102. The patient 102 enters responses to the questions using an input device such as the touchscreen input.

In some embodiments, the telehealth device 104 records data generated by one or more patient monitor devices 106. The patient monitor devices 106 generate measurements of one or more bodily indicators in the patient 102. A non-exclusive list of patient monitor devices includes heart rate monitors, thermometers, blood pressure monitors, blood sugar meters, respiration monitors, and the like. In some embodiments the patient monitor devices 106 are communicatively linked to the telehealth device 104 and transmit data pertaining to the patient 102 to the telehealth device. In other embodiments, the telehealth device 104 prompts the patient 102 to input measurements from the monitor devices into the telehealth device 104 manually.

The telehealth device 104 sends medical data collected from the patient 102 and patient monitor devices 106 to the telehealth analysis system 112 through a data network such as the Internet 108. The telehealth analysis system 112 includes one or more network interface devices 116 and processor 118, and a memory 120. The telehealth analysis system receives the medical data via one or more network interface devices 116 and a processor 118 identifies the content of the received medical data and stores the medical data in a memory 120.

An exemplary embodiment of the telehealth analysis system 112 is a server computing system including one or more hardware processors 118 such as central processing units (CPUs) from the x86 or ARM families. The memory 120 includes both random access memory (RAM) and data storage devices such as hard drives and solid state storage devices. The server includes one or more network interfaces 116 including wired and wireless network adapters that receive data from the telehealth device 104, and store the time series medical data 124 in a database held in the memory. In a typical configuration, a single telehealth analysis system 112 receives data from a plurality of telehealth devices assigned to multiple patients. Each set of medical data includes values corresponding to multiple variables associated with the patient. Variable data include answers to questions that the patient 102 inputs into the telehealth device 104, and data from the monitoring devices 106. When a datum is missing from the medical data, a special identifier such as a null value is stored in the medical database 124. In a partial record, a single datum or a subset of the data is missing, but at least one other datum is observed in the medical data. The estimated value database 128 stores an estimated value associated with the patient, time, and medical variable of the missing data. The processor 118 stores a series of medical data 124 in the memory 120 in association with an identifier corresponding to the individual patient 102 and in association with a time at which each set of medical data are recorded by the telehealth device 104.

During the course of medical treatment, one or more healthcare providers, such as doctors and nurses, access medical data for the patient 102. The healthcare providers use a terminal device 144 to access stored medical data for the patient 102. Various embodiments of the healthcare provider terminal 144 include desktop and notebook computers, smartphones, personal digital assistants (PDAs), tablet computers, or any computing device that is configured to display medical data. In one embodiment, the telehealth system 112 executes a web server application, and a web browser application executed on the healthcare provider terminal requests medical data for the patient 102 from the web server through a local area network (LAN) or wide area network (WAN) 140, where the WAN can also be the Internet 108. The healthcare provider terminal 144 presents both observed data values held in the database 124, and estimated values for missing medical data held in the database 128. In some embodiments the healthcare analysis system 112 generates an indicator that enables the healthcare provider to distinguish the estimated data from the recorded data. For example, the estimated data can be presented with a different color or font from the directly recorded medical data 124.

Figure 2:
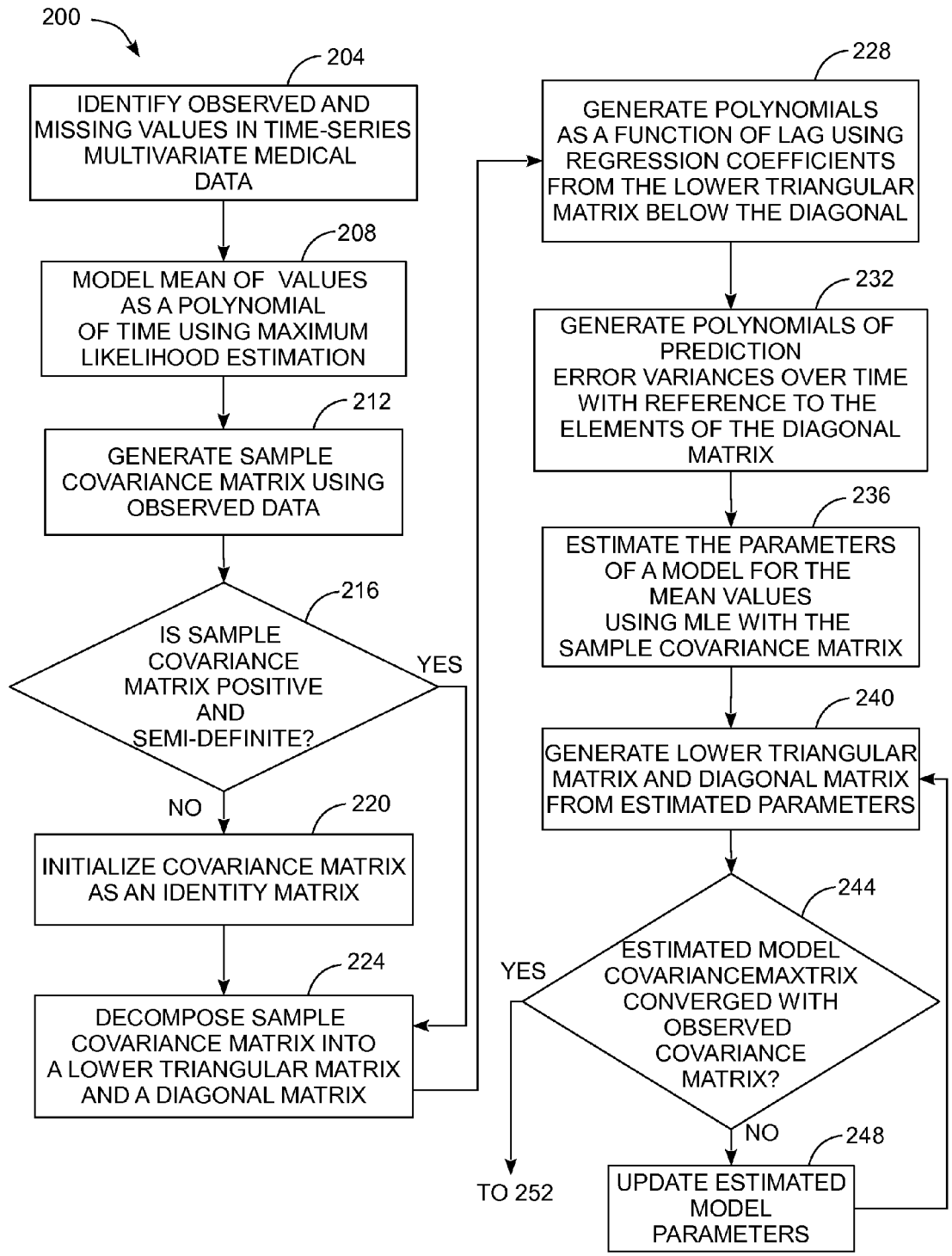
FIG. 2 is a block diagram of a process for estimating missing values in medical data corresponding to a patient.
Figure 2:
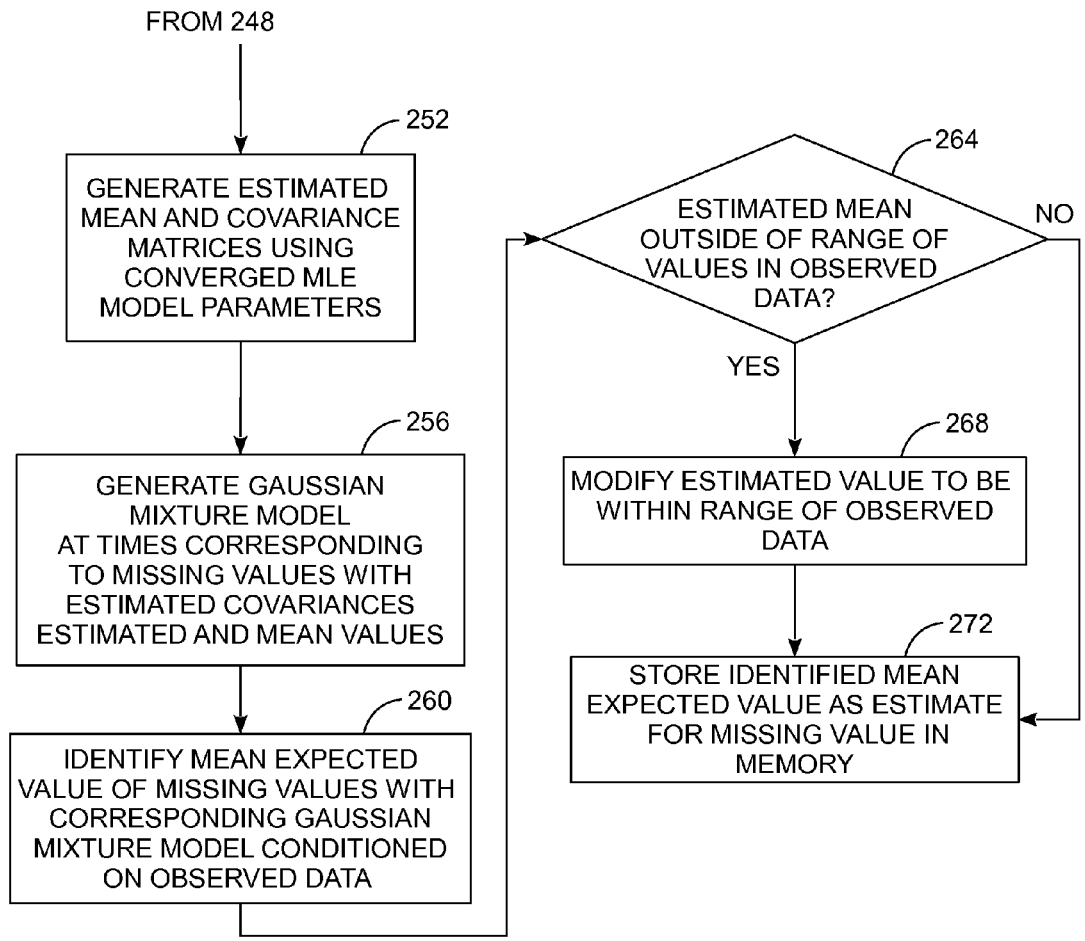

FIG. 2 depicts a process 200 for identifying estimates of missing medical information in a series of medical data generated in a telehealth device. As used in this document, a reference to a process performing or doing some function or event refers to a controller configured with programmed instructions and electronic components to implement the process performing or doing the function or event. Process 200 references the telehealth system 100 of FIG. 1 for illustrative purposes. The processor 118 executes stored program instructions 132 retrieved from the memory 120 to perform the operations described in process 200. Process 200 begins by identifying observed and missing values in time series multivariate medical data (block 204). During a course of treatment, the telemedical device 104 collects various different data from the patient 102, and collects the same pieces of data from the patient at multiple different times. For example, the telehealth device 104 can ask the same question of the patient 102 on a daily basis. Each question or recorded measurement from a monitoring device is modeled as an individual series of random variables, and the telehealth device 104 collects data corresponding to multiple series of random variables from the patient 102 over time.

In some cases, the telemedical device 104 collects multivariate data consistently at regular intervals, while in other cases a particular datum may be missing from some intervals. When the telehealth system 104 generates data corresponding to one of the variables at a given time, then the generated data includes an "observed" value. The observed value is a realization of one potential value for the random variable representing the medical data variable at a particular time. For example, one series of medical data for the patient 102 could be temperature. The temperature of the patient varies over time, and the telehealth system 104 generates readings of the temperature at regular intervals. The temperature of the patient during each time is modeled as a random variable, such as a Gaussian random variable. When the telehealth device 104 receives a temperature reading from a thermometer, the identified temperature of the patient 102 is a single realization of the random variable. If, however, the thermometer data are not available at a particular time, process 200 generates an estimate of the missing temperature based on the random variable used to model temperature, as well as one or more additional medical data values that are observed at the time when the temperature value is missing in a partial record. Missing data may occur simply because the patient 102 does not answer one or more questions generated by the telehealth device 104. In many cases, the telehealth device 104 collects a partial set of medical data and sends the partial set of data to the telehealth analysis system 112.

Figure 3A:
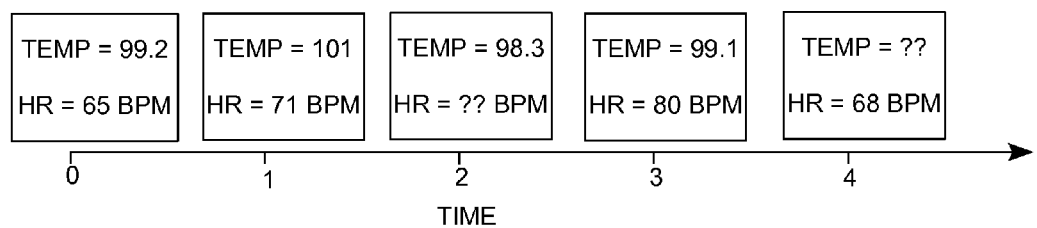
FIG. 3A is a diagram depicting medical data, including partially complete medical data, corresponding to a single patient over multiple time periods.

FIG. 3A depicts an exemplary time series of medical data collected from a patient. In FIG. 3A the telehealth device 104 collects the temperature and heart rate of patient 102 at regular intervals over time. The temperature and heart rate are two variables in the multivariate medical data. The telehealth device 104 collects both the temperature and heart rate during time intervals 0, 1, and 3. During time periods 2 and 4, however, the telehealth device only collects the temperature and heart rate for the patient, respectively. When the telehealth device 104 only collects a portion of the multivariate medical data, the telehealth device 104 generates a null value or other data that indicate a value for one or more of the variables is missing. The telehealth analysis system 112 stores the partially collected medical data in the recorded medical data database 124 with a time stamp identifying when the medical data were recorded. The telehealth analysis system 112 also records the missing values and time stamps of the missing values in the estimated values database 128. In process 200, the telehealth analysis system 112 separates or partitions the missing data from the observed data and generating the missing data based on default null values and time stamps for the missing data.

The telehealth system 112 also identifies missing data when different medical data variables are measured at different frequencies. For example, the telehealth device 104 can collect data from a heart rate monitor coupled to the patient 102 one or more times each minute. In a second variable, the telehealth device 104 asks the patient if he or she has experienced shortness of breath during the past day. Since the question is only generated once per day, the telehealth device 104 identifies that the answer to the question is missing when sending data corresponding to the heart rate to the telehealth analysis system 112.

Figure 4:
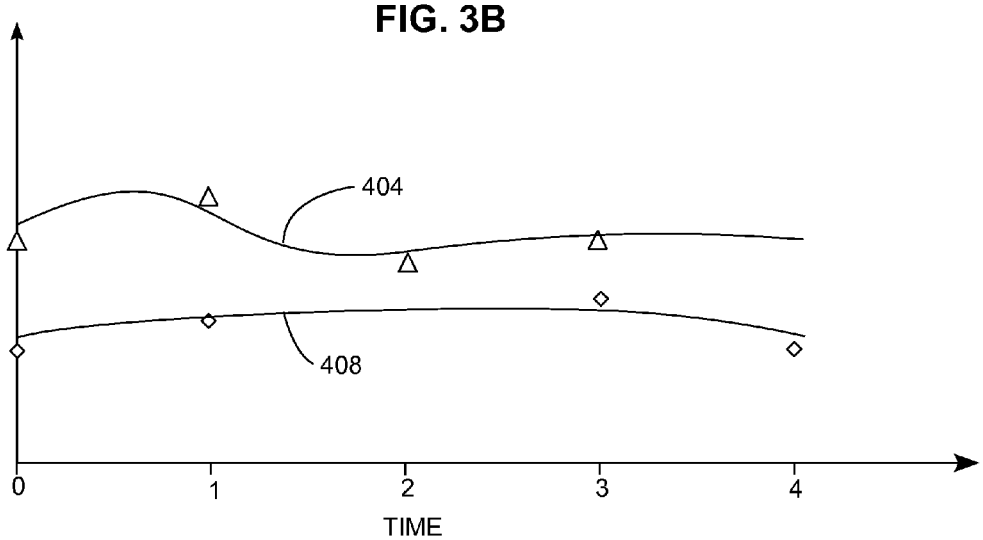
FIG. 4 is a diagram depicting polynomial curves that fit the values of observed medical data for a patient.

Process 200 generates a model for the mean as a polynomial of time (block 208). Using the observed data, the parameters $\beta$ of the mean model, are estimated first. In one embodiment, the parameters $\beta$ are estimated with a least squares estimation method. Other embodiments use splines and first or higher order polynomials to generate a fit through the mean values of the random variables. The curve fit to the mean values ignores time values in the longitudinal data when a value is missing from one of the series of random variables. FIG. 4 depicts a curve fit 404 through mean values of temperature data and another curve fit 408 through the mean values of heart rate data from FIG. 3A.

Process 200 then generates a sample covariance matrix Q of the observed data stored in the recorded medical database 124 for the patient 102 (block 212). In the context of process 200, the term "sample covariance matrix", refers to an N×N matrix Q containing covariance values between vectors of random variables representing N different time periods when medical data are collected. Process 200 uses the medical data that are observed for each of the random variable vectors $y_n$ and ignores missing values to generate the sample covariance matrix Q.

Each of the N random variable vectors in the sample covariance matrix Q includes random variables corresponding to the multivariate data collected during each time. If Q is not a positive semi-definite matrix (block 216) then process 200 initializes Q by assuming that Q is a N×N identity matrix (block 220). If the original sample covariance matrix Q is a positive semi-definite matrix (block 216), then process 200 continues using the original sample covariance matrix Q.

After generation of the sample covariance matrix Q, process 200 decomposes the sample covariance matrix with Cholesky decomposition (block 224). The Cholesky decomposition generates a unit lower triangular matrix, T and a diagonal matrix, D with positive entries. The below-diagonal entries of the unit lower triangular matrix T are the negatives of the regression coefficients $\phi_n$ when each response is regressed onto previously observed values and the diagonal elements of D are the prediction error variances $\sigma_n^2$ of the regression model of each response onto previously observed values at each time period n=1, 2, ..., N. FIG. 5 depicts an example of a lower-triangular matrix T generated for the random vectors $y_0$-$y_4$. The dimensions of the sample covariance matrix and corresponding lower-triangle matrix T are determined by the number of previous medical data samples generated over time. Thus, for $y_4$ the sample covariance matrix and corresponding lower-triangle matrix T are 5×5 matrices, while for $y_3$ the sample covariance matrix and lower-triangle matrix T are 4×4 matrices. Process 200 identifies the regression coefficients $\phi_n$ obtained from the lower triangular matrix T as a function of the lag to choose a polynomial of lags as a model for the regression coefficients. Similarly, process 200 a polynomial in time function for the log of the elements of diagonal matrix D from the logarithm of the prediction error variances $\sigma_n^2$ for each of the random variable vectors $y_n$ with respect to time.

Process 200 generates a polynomial curve fit as a function of lag for each vector of random variables $y_n$ using the regression coefficients $\phi_n$ from the lower-triangular matrix T (block 228). In one embodiment, each regression coefficient $\phi_n$ includes a vector of coefficient values in which each coefficient value corresponds to one random variable in the corresponding $y_n$ random variable vector. The regression coefficients $\phi_0$-$\phi_{N-1}$ are coefficients in a polynomial curve fit of the change in covariance as a function of lag.

As used herein, lag refers to the effect of the covariance of previous time periods on the covariance of a current time period. For example, a typical lag polynomial uses the regression coefficients to assign relative weights to the covariance values of preceding time periods for the $y_n$ random variable vectors. In some embodiments, the lag polynomials assign a higher magnitude to the value of regression coefficients corresponding to time periods that are close to one another and reduces the magnitude of the other regression coefficients to discount time periods that are more remote to a current time period. For example, in FIG. 3A if the current time period is time period 4, then the regression coefficient $\phi_3$ from time period 3 has a greater magnitude on the estimation of the covariance of the random variables in $y_4$ than the regression coefficient $\phi_0$, which corresponds to the vector $y_0$ that occurred further in the past.

In addition to identifying a polynomial with respect to lag that describes the changes in covariance for the random vectors $y_n$, process 200 generates a polynomial curve fit of the prediction error variances $\sigma_n^2$ for each of the random vectors $y_n$ with respect to time (block 232). The prediction error variances $\sigma_n^2$ represent the variances of measured errors $\epsilon_n$ between the curve fit of the lag polynomials generated using the regression coefficients $\phi_n$ and the observed values for the random variable vectors $y_n$. The errors $\epsilon_n$ are identified as a cross-product multiplication of the triangular matrix T and the random variable vectors $y_n$ arranged in a columnar matrix Y as depicted in FIG. 5. The diagonal matrix D is equivalent to the diagonal of a covariance matrix for the measured errors depicted in FIG. 6, where each element $\sigma_n^2$ in the diagonal is the variance for one of the error terms, $\epsilon_n$. Alternatively, the following equation identifies the diagonal matrix D:D=TCov(Y)T' where T is the unit lower triangular matrix of the regression coefficients $\phi$ and T' is the transpose of the triangular matrix T. Each identified variance value $\sigma_n^2$ corresponds to the variance of errors in one of the random vectors $y_n$. Since the random vectors $y_n$ correspond to a single time, process 200 generates a relationship between the variance values $\sigma_n^2$ and time. Process 200 generates a polynomial curve fit through the variance values $\sigma_n^2$ that estimates the variance value for the components of the random vectors $y_n$ at different times. In one embodiment, process 200 generates a curve of the natural logarithm $\log_e(\sigma_n^2)$ values of the variances over time instead of the original values $\sigma_n^2$ of the variances.

Once models for the covariance structure are formulated, the parameters $(\lambda,\gamma)$ for (T, D) are estimated using the maximum likelihood estimation (MLE) for one set of model parameters $\beta$ (block 236). In one embodiment, the process 200 performs the MLE of parameters $(\lambda,\gamma)$ corresponding to the parameters of the models for T and D. Using the estimates of $\lambda$ and $\gamma$, process 200 constructs the estimated matrices of T and D as $\hat{T}(\hat{\lambda})$ and $\hat{D}(\hat{\gamma})$, respectively (block 240). Then using the equation $\text{Cov}(Y)=\Sigma=T^{-1}D(T')^{-1}$, process 200 generates an estimated covariance matrix $\hat{\Sigma}$. In one embodiment, process 200 generates the MLE estimate for the covariance matrix, which is guaranteed to be positive definite. Using the estimated $\hat{\Sigma}$, process 200 updates the model parameters $\beta$ and the model generates updated values for $(\lambda,\gamma)$ (block 248). Process 200 iterates to generate additional covariance matrices with the updated model parameter values $\beta$ (block 240) until the estimates of the parameters produce a covariance matrix that converges with the observed parameters in the sample covariance matrix (block 244).

The identified parameter values for the regression coefficients $\phi_n$ and the variances $\sigma_n^2$ enable process 200 to generate curve fits that identify the covariance for each random variable vector $y_n$ at any time n when medical data are recorded from the patient. Process 200 identifies the covariance for a particular random variable vector $y_n$ using both the lag polynomial, which has the regression coefficients $\phi_n$ generated for the previous n covariance values, and the time valued polynomial, which is generated for the variance of each of the random variables at the time corresponding to the variance $\sigma_n^2$ of the components of the vector $y_n$. The covariance for the random vector $y_n$ is identified based on the relationships between variables, and also on changes over time.

Figure 3B:
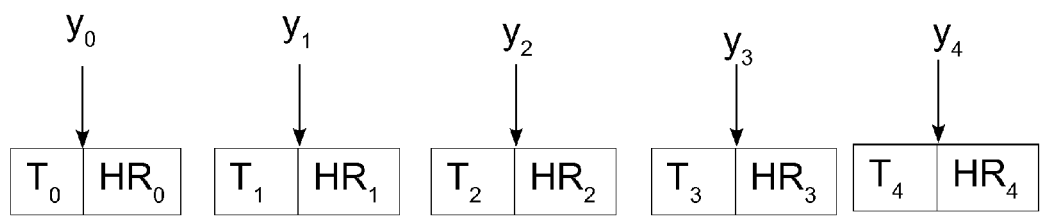
FIG. 3B is a diagram depicting vectors of random variables corresponding to the medical data in FIG. 3A.

Process 200 generates the estimated covariance matrix for the random variables that takes into account the changes in medical condition that the patient 102 experiences over time and changes in the covariance of different medical data that the patient experiences. As described in more detail below, the generated covariance estimate enables more accurate estimation of missing medical data values based on the condition of the patient 102 when the partial medical data are generated. Referring to FIG. 3A and FIG. 3B, the random variable vectors $y_0$-$y_4$ correspond to the time periods 0-4 when data are collected from the patient. More generally, one of the N random vectors is denoted as $y_n$. Each of the random variable vectors $y_0$-$y_4$ further includes random variables representing each of the variables measured by the telehealth device. In the example of FIG. 3B, each of the vectors $y_0$-$y_4$ includes two random variables, $T_n$ and $HR_n$ that correspond to the temperature and heart rate of the patient 102, respectively, during each of the N time periods. In different sets of medical data for different patients, the number of random variable vectors y is selected based on the number of multivariate observations in the health data collected for the patient. Each of the random vectors y includes at least two random variables, which are exemplified as random variables corresponding to temperature and heart rate in FIG. 3A and FIG. 3B. A population of patients with telehealth devices answers a variety of different questions to provide sets of medical data to the telehealth analysis system 112 based on the medical condition of each patient and treatment. Thus, each vector of random variables $y_n$ can include a wide range of variables corresponding to the responses for each patient over time. Some embodiments that include a large number of medical data samples use a limited number of random variable vectors corresponding to the earlier samples to generate the covariance matrix. For example, if a series of 1,000 samples precedes the most current set of medical data, then one embodiment of process 200 uses the random variables from the 100 most recent medical data samples to generate a 100×100 matrix.

After identifying the model parameters β, process 200 generates mean and covariance matrices using the estimated model (block 252). To identify an estimate of a missing value in the medical data, process 200 identifies, in one embodiment, a Gaussian mixture model corresponding to one of the vectors $y_n$ that includes only partially identified medical information (block 256). In general, a Gaussian mixture model includes Gaussian distributions of two or more random variables and can be defined with a vector μ of mean values for each random variable and the covariances Σ of the random variables. A multivariate Gaussian distribution is one example of a Gaussian mixture model. Process 200 generates estimated values $\hat{T}$ and $\hat{D}$ corresponding to the time n using the polynomials generated with reference to the estimated model. Process 200 generates estimated mean values $\hat{\mu}$ for each of the random variables with the estimated regression coefficients in $\hat{T}$ as a function of lag at the times of one or more missing values. The following equation provides the estimated covariance $\hat{\Sigma}: \hat{\Sigma} = \hat{T}^{-1} \hat{D} \hat{T}^{-1'}$ where $\hat{T}^{-1}$ is the inverse matrix of the estimated lower triangular matrix $\hat{T}$ and $\hat{T}^{-1'}$ is the transposition of the inverse matrix $\hat{T}^{-1}$. The Gaussian mixture model of the random variable vectors Y is expressed as ~N $(\hat{\mu},\hat{\Sigma})$.

After generating the Gaussian mixture model, process 200 identifies a missing data value at time n using the Gaussian mixture model conditioned on data values that are observed at time n (block 260). For example, in FIG. 3A, at time 4 the heart rate variable has an identified value of 68 beats per minute (BPM), but the temperature value is missing. Process 200 identifies an estimated sample value (e.g., mean, mode, or other appropriately sampled value) for the temperature. In one embodiment, process 200 identifies the mean $\hat{\mu}_T$ with the Gaussian mixture model generated for time n=4 conditioned on the identified value for the heart rate: $Y_{(T|HR)} = \hat{\mu}_{(T|HR)}$. Thus an estimated value for the missing temperature value is imputed to be the estimated mean value $\hat{\mu}_{(T|HR)}$.

After identification of the estimate for the missing value in the medical data, process 200 identifies whether the estimated value is greater than or less than the range of observed values for the random variable that are observed in the medical data (block 264). For example, in FIG. 3A, the minimum and maximum values for temperature observed in the data are 98.3° and 101°, respectively. If the estimated value of $\hat{\mu}_{(T|HR)}$ is between 98.3° and 101°, then the estimated value $\hat{\mu}_{(T|HR)}$ is stored in the estimated values database 128 in the memory 120 (block 272). If however, the value of $\hat{\mu}_{(T|HR)}$ is below 98.3° or above 101°, then process 200 modifies the value of $\hat{\mu}_{(T|HR)}$ to be within the range of observed values for the temperature of the patient (block 268). In one embodiment, process 200 sets the value of $\hat{\mu}_{(T|HR)}$ to be the minimum observed value (98.3°) when $\hat{\mu}_{(T|HR)}$ is below the range of observed values, and process 200 sets the value of $\hat{\mu}_{(T|HR)}$ to be the maximum observed value (101°) when $\hat{\mu}_{(T|HR)}$ is above the range of observed values. Process 200 stores the modified estimate value in the estimated values database 128 in the memory 120 (block 272). Process 200 modifies estimated values that fall outside of the range of observed values in the medical data to prevent estimates of missing values for the medical data from conflicting with the observed data.

The telehealth analysis system 112 performs process 200 to generate estimates of missing medical data values while accounting for changes in the condition of the patient 102 that occur over time. Process 200 generates, in one embodiment, the Gaussian mixture model in a non-stationary manner. That is to say, instead of assuming that a single Gaussian distribution describes distribution of multiple random variables in the medical data for the patient 102 at all times, process 200 instead identifies the changes in both the center (mean) and shape (covariances) of the Gaussian mixture model that occur as the medical condition of the patient changes. The non-stationary Gaussian distribution generates more accurate estimates of missing medical data values based on both the previously observed medical data for the patient, and on the values that are observed in the partially complete medical data.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following claims.

We claim:
1. A method for estimating a value of a missing datum in a multivariate time series of data comprising:
generating a plurality of medical data sets for a patient with a telehealth device, each medical data set being generated at one time period in a plurality of times;
storing the plurality of medical data sets for the patient in a memory in association with the time at which each medical data set is generated with a controller communicatively coupled to the memory;
retrieving a plurality of variables in the plurality of medical data sets corresponding to the plurality of times from the memory with the controller;
detecting a missing datum and a time period of the missing datum corresponding to one variable in the plurality of variables for one of the medical data sets and one time in the plurality of times in the retrieved data with the controller;
generating data corresponding to a function of a mean of each of the plurality of variables with respect to time with the controller;
identifying, with the controller, a plurality of random variable vectors with reference to the plurality of times, each random variable vector including a plurality of random variables that correspond to each of the plurality of variables;
generating data corresponding to a covariance matrix of the plurality of random variable vectors with the controller;
generating, with the controller, a conditional Gaussian mixture model corresponding to the one time of the missing datum with reference to the polynomial of the mean of each variable at the one time, the covariance matrix, and the data corresponding to at least one variable in the plurality of variables other than the one variable;
identifying an estimated value for the missing datum with reference to the conditional Gaussian mixture model with the controller; and
storing the estimated value for the missing datum in the memory with the controller to enable processing of the plurality of medical data sets for the patient including the data associated with the plurality of variables corresponding to the plurality of times, the estimated value being stored with reference to the one variable and the one time of the missing datum.

2. The method of claim 1, the detecting of the missing datum further comprising:
partitioning the data into a plurality of observed values and a plurality of missing values;
storing default values for the missing values in the memory; and
identifying a plurality of time periods corresponding to time periods of the missing values.

3. The method of claim 1, the identification of the estimated value for the missing datum further comprising:
identifying with the controller a sampled value, a mean, or a mode of the conditional Gaussian mixture model as the estimated value for the missing datum.

4. The method of claim 1 further comprising:
identifying with the controller a range of values corresponding to the one variable at times other than the one time;
identifying with the controller a maximum value in the identified range of values as a second estimated value for the missing datum in response to the identified estimated value for the missing datum being greater than the maximum value in the range of values;
identifying with the controller a minimum value in the range of values as the second estimated value for the missing datum in response to the identified estimated value for the missing datum being less than the minimum value in the range of values; and
storing with the controller the second estimated value for the missing datum in the memory instead of the identified estimated value with reference to the one variable and the one time of the missing datum in response to the identified estimated value being greater than the maximum value in the range or less than the minimum value in the range.

5. The method of claim 1 further comprising:
decomposing the covariance matrix into a triangular matrix of regression coefficients and a diagonal matrix of variance values with the controller;
generating a plurality of parameters corresponding to the regression coefficients in the triangular matrix with the controller;
generating a plurality of parameters corresponding to the variance values in the diagonal matrix with the controller;
generating a covariance model with reference to the plurality of parameters corresponding to the regression coefficients in the triangular matrix and the plurality of parameters corresponding to the variance values in the diagonal matrix with the controller; and
generating the conditional Gaussian mixture model with reference to a polynomial of a plurality of lags generated from the covariance model and a polynomial of the plurality of variances generated from the covariance model with the controller.

6. The method of claim 5, wherein the decomposition of the covariance matrix is a Cholesky decomposition.

7. The method of claim 5, the controller generating the covariance model with a maximum likelihood estimation of the data corresponding to the covariance matrix of the plurality of random variable vectors.

8. The method of claim 1, the controller generating the data corresponding to the function of the mean of each variable in the plurality of variables with respect to time.

9. The method of claim 1 further comprising:
generating with a patient health monitoring system medical data corresponding to the plurality of variables, the plurality of variables corresponding to medical data for a patient;
transmitting the medical data and a timestamp associated with the medical data from the patient health monitoring system to the controller;
storing the medical data transmitted from the patient health monitoring system in the memory with the controller, each datum in the transmitted data being stored in the memory in association with a variable in the plurality of variables for the patient and a time associated with the timestamp;
detecting with the controller a missing datum corresponding to a variable in the plurality of variables for the patient; and
storing with the controller an identifier indicating that datum is missing for the variable at the time associated with the timestamp.

10. A healthcare analysis system comprising:
a memory configured to store recorded values of a plurality of variables corresponding to medical data of a patient generated at a plurality of times;
an output device configured to display the recorded values for a healthcare provider; and
a controller operatively connected to the memory and the output, the controller being configured to:
detect a missing datum corresponding to one variable in the plurality of variables and one time in the plurality of times in the recorded values in the memory;
generate data corresponding to a polynomial of a mean of each of the plurality of variables with respect to time;
identify a plurality of random variable vectors with reference to the plurality of times, each random variable vector including a plurality of random variables that correspond to each of the plurality of variables;
generate data corresponding to a covariance matrix of the plurality of random variable vectors;
generate a conditional Gaussian mixture model corresponding to the one time of the missing datum with reference to the polynomial of the mean of each variable at the one time, the covariance matrix, and the data corresponding to at least one variable in the plurality of variables other than the one variable;
identify an estimated value for the missing datum with reference to the conditional Gaussian mixture model;
store the estimated value for the missing datum in the memory with the controller to enable processing of the data associated with the plurality of variables corresponding to the plurality of times, the estimated value being stored with reference to the one variable and the one time of the missing datum; and
generate a display of the recorded values of the plurality of variables and the estimated value for the missing datum with the output device.

11. The system of claim 10, the controller being further configured to:
identify a mean, a mode, or a sampled value of the conditional Gaussian mixture model as the estimated value for the missing datum.

12. The system of claim 10, the controller being further configured to:
identify a range of values corresponding to the one variable retrieved from the memory at times other than the one time;

identify a maximum value in the identified range of values as a second estimated value for the missing datum in response to the identified estimated value for the missing datum being greater than the maximum value in the range of values;

identify a minimum value in the range of values as the second estimated value for the missing datum in response to the identified estimated value for the missing datum being less than the minimum value in the range of values; and store the second estimated value for the missing datum in the memory instead of the identified estimated value with reference to the one variable and the one time of the missing datum in response to the identified estimated value being greater than the maximum value in the range or less than the minimum value in the range.

13. The system of claim 10, the controller being further configured to:

decompose the covariance matrix into a triangular matrix of regression coefficients and a diagonal matrix of variance values;

generate a plurality of parameters corresponding to the regression coefficients in the triangular matrix;

generate a plurality of parameters corresponding to the variance values in the diagonal matrix;

generate a covariance model with reference to the plurality of parameters corresponding to the regression coefficients in the triangular matrix and the plurality of parameters corresponding to the variance values in the diagonal matrix; and generate the conditional Gaussian mixture model with reference to a polynomial of a plurality of lags generated from the covariance model and a polynomial of the plurality of variances generated from the covariance model.

14. The system of claim 13, wherein the controller generates the triangular matrix with a Cholesky decomposition.

15. The system of claim 13, wherein the controller generates data corresponding to the polynomial of the plurality of variances with respect to time with a maximum likelihood estimation.

16. The system of claim 10, the controller generating the data corresponding to the polynomial of the mean of each variable in the plurality of variables with respect to time with a maximum likelihood estimation.

17. The system of claim 10 further comprising:

a patient health monitoring system configured to:

generate medical data corresponding to the plurality of variables;

transmit the medical data and a timestamp associated with the medical data from the patient health monitoring system to the controller; and the controller being further configured to:

store the medical data transmitted from the patient health monitoring system in the memory, each datum in the transmitted data being stored in the memory in association with a variable in the plurality of variables for the patient and a time associated with the timestamp;

detect a missing datum corresponding to a variable in the plurality of variables for the patient; and store an identifier indicating that datum is missing for the variable at the time associated with the timestamp.

* * * * *